US008923481B2

(12) United States Patent
Schubert et al.

(10) Patent No.: US 8,923,481 B2
(45) Date of Patent: Dec. 30, 2014

(54) METHODS TO PERFORM BACKSCATTER INSPECTION OF COMPLEX TARGETS IN CONFINED SPACES

(75) Inventors: Jeffrey R. Schubert, Somerville, MA (US); John P. Handy, Nashua, NH (US); Richard L. Schueller, Chelmsford, MA (US); Terry Lee McElroy, Arlington, MA (US); David C. Walazek, Billerica, MA (US); William J. Baukus, Nashua, NH (US)

(73) Assignee: American Science and Engineering, Inc., Billerica, MA (US)

( * ) Notice: Subject to any disclaimer, the term of this patent is extended or adjusted under 35 U.S.C. 154(b) by 307 days.

(21) Appl. No.: 13/446,790

(22) Filed: Apr. 13, 2012
(Under 37 CFR 1.47)

(65) Prior Publication Data

US 2013/0101090 A1    Apr. 25, 2013

Related U.S. Application Data

(60) Provisional application No. 61/476,002, filed on Apr. 15, 2011.

(51) Int. Cl.

| | |
|---|---|
| *G01N 23/201* | (2006.01) |
| *H05G 1/02* | (2006.01) |
| *A61B 6/10* | (2006.01) |
| *F16P 3/14* | (2006.01) |
| *G01N 23/203* | (2006.01) |

(52) U.S. Cl.
CPC .................................. *G01N 23/203* (2013.01)
USPC ........... 378/86; 378/193; 378/205; 250/208.4

(58) Field of Classification Search
USPC ....................... 378/70, 76, 79–81, 86–90, 95, 378/162–164, 189, 193–198, 204, 205, 378/210; 250/370.01, 370.08, 370.09, 250/370.1, 206, 208.4, 491.1, 522.1, 526; 356/337–343, 237.1, 240.1, 241.1, 356/241.3, 241.4, 241.5, 241.6, 256
See application file for complete search history.

(56) References Cited

U.S. PATENT DOCUMENTS 6,637,266 B1 *  10/2003  Froom ........................... 73/583
7,508,910 B2 *   3/2009  Safai et al. ....................... 378/57
(Continued)

OTHER PUBLICATIONS

Authorized Officer: Hyeong Keun Kim, Notification of Transmittal of the International Search Report and the Written Opinion of the International Searching Authority, or the Declaration, PCT/US2012/033581, Date of Mailing: Oct. 31, 2012, 10 pages.

(Continued)

*Primary Examiner* — Anastasia Midkiff
(74) *Attorney, Agent, or Firm* — Sunstein Kann Murphy & Timbers LLP

(57) ABSTRACT

Embodiments of backscatter inspection systems include features to enable inspection of irregular surfaces, tight spacer, and other hard-to-reach places. Some embodiments include arms that maneuver a scan head with at least three degrees of freedom, and some embodiments include arms that maneuver a scan head with at least seven degrees of freedom. Some embodiments include proximity detectors on a scan head or base, detect contact with an object being inspected, and to slow or stop the motion of the system accordingly. Some compact embodiments scan the interior of an object from within, and include a rotating, low-energy source of penetrating radiation, and at least one backscatter detector, which may be stationary, or may rotate with the source.

14 Claims, 10 Drawing Sheets

(56) References Cited

U.S. PATENT DOCUMENTS

| | | | |
|---|---|---|---|
| 7,623,626 B2 | 11/2009 | Safai et al. ................. 378/87 |
| 8,033,724 B2 * | 10/2011 | Edwards et al. ............ 378/194 |
| 8,483,356 B2 | 7/2013 | Bendahan ................... 378/57 |
| 2003/0043964 A1 * | 3/2003 | Sorenson .................... 378/58 |
| 2006/0198498 A1 * | 9/2006 | Birdwell et al. ............ 378/204 |
| 2007/0098142 A1 | 5/2007 | Rothschild et al. ......... 378/57 |
| 2010/0061509 A1 | 3/2010 | D'Ambrosio et al. ...... 378/62 |
| 2011/0103548 A1 * | 5/2011 | Bendahan ................... 378/57 |

OTHER PUBLICATIONS

Tuytschaevers, T.J., Amendment Under Article 19, PCT/US2012/033581, Dec. 20, 2012, 10 pages.

Authorized Officer: Philippe Bécamel, Notification Concerning Transmittal of International Preliminary Report on Patentability, PCT/US2012/033581, Date of Mailing: Oct. 31, 2012, 6 pages.

Hector Javier Sanchez Vargas, Instituto Mexicano de la Propiedad Industrial, Office action dated Jul. 11, 2014, Mexican patent application No. MX/A/2013/011843, 3 pages.

* cited by examiner

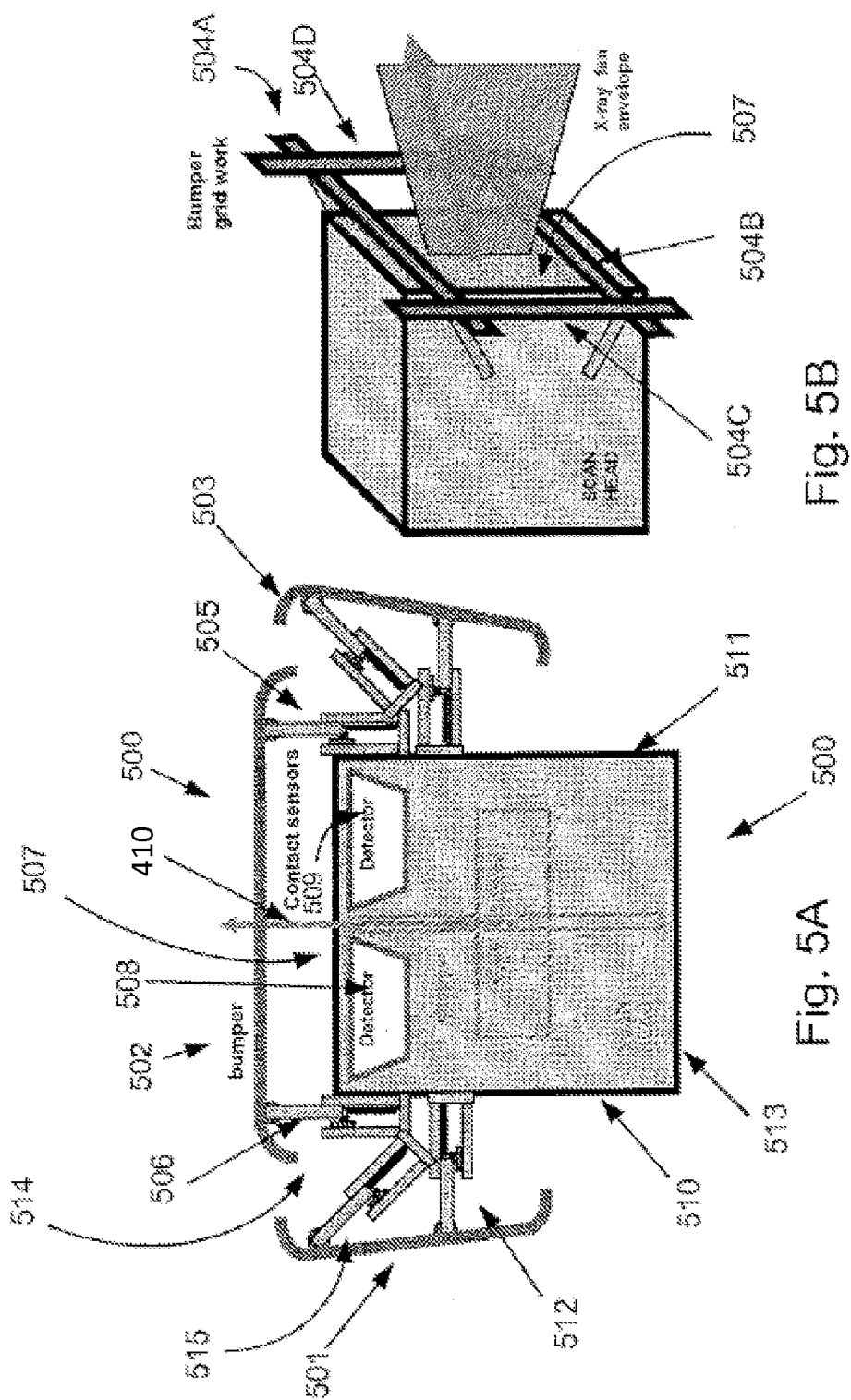

METHODS TO PERFORM BACKSCATTER INSPECTION OF COMPLEX TARGETS IN CONFINED SPACES

TECHNICAL FIELD

This patent application claims priority from provisional U.S. patent application No. 61/476,002, filed Apr. 15, 2011, entitled, "Methods to Perform Backscatter Inspection of Complex Targets in Confined Spaces" and naming Jeffrey R. Schubert, John P. Handy, Richard L. Schueller, Terry Lee McElroy, David C. Walazek, and William J. Baukus as inventors, the disclosure of which is incorporated herein, in its entirety, by reference.

TECHNICAL FIELD

The present invention relates to inspection equipment based on detection of backscattered penetrating radiation, and more particularly to inspection equipment employed in the inspection of aircraft with x-rays.

BACKGROUND ART

It is known in the prior art to inspect an object by illuminating it with penetrating radiation, such as x-rays, for example. Some of the radiation may pass through the object, and some may be absorbed or scattered by the object. Of incident radiation scattered in all directions, scattered radiation back in the general direction from which it was incident may be referred to as backscatter radiation. Such scattered radiation may pass into a detector (which may be referred to herein as a "scatter detector"), and some portion of that scattered radiation will be detected by the scatter detector.

Scattered radiation highlights features, including concealed contraband or plastic explosives, that are characterized by a lower atomic number, whereas penetrating radiation is more likely to be absorbed in the bulk of higher-atomic number material, since photo-electric absorption increases very rapidly (as between the fourth and fifth power) with atomic number. The metallic body of an aircraft will highly absorb x-rays, whereas contraband materials will be more evident in x-ray backscatter.

Since, for a fixed detection efficiency per unit area, the signal-to-noise ratio increases with solid angle subtended by the scatter detector, backscatter systems tend to be ponderous and not well suited to inspection within confined area. This has had the effect of limiting the applicability of backscatter inspection modalities.

SUMMARY OF EMBODIMENTS

In a first embodiment of the invention there is provided a nimbly positionable backscatter inspection system, the system including a base; an arm coupled to the base, the arm comprising a first segment, a second segment, and a third segment, as well as a first movable joint coupling the first segment to the second segment, and a second movable joint coupling the second segment to the third segment; a scan head coupled to the third segment, the scan head including a source of penetrating radiation for generating a pencil beam of penetrating radiation, the pencil beam characterized by a beam axis, and a primary detector configured to detect scattered penetrating radiation; wherein the scan head is movable in at least 3 to 7 degrees of freedom with respect to the base, and the system is capable of capturing backscatter radiation in a plurality of orientations by moving the scan head while the first segment remains stationary with respect to the base.

In some embodiments, at least one of the first and second segments is extendable. In some embodiments, the third segment has an axis along its length, and the scan head is rotatable around the axis. In some embodiments, the size of the scan head is such that the scan head is adapted to be contained within an object being inspected.

In another embodiment, a method of capturing a backscatter image derived by irradiating a surface that is interior to an object includes positioning a backscatter inspection system adjacent to the object, the backscatter inspection system having a base, an extendable arm secured to the base, the arm comprising at least two segments coupled by a movable joint, and a scan head at a distal end of the arm; manipulating the arm to extend from the base through a portal in the object to a volume interior to the object; irradiating the surface interior to the object with a pencil beam of penetrating radiation; receiving backscatter radiation at the scan head; and processing the backscatter radiation to form an image of a portion of an interior volume of the object. In some embodiments, the method also includes manipulating the scan head to sequentially orient the scan head in a plurality of orientations within the volume interior to the object.

In another embodiment, a movable backscatter inspection system for interrogating an object includes a movable base; a source of a pencil beam of penetrating radiation, the source having an axis of emission and coupled to the base; a scan head coupled to the base, the scan head comprising at least one detector at a location not on the axis of emission and oriented to receive penetrating radiation scattered by the object; and at least one proximity sensor coupled to the base, and arranged to detect a predefined separation between the location and the object.

In some embodiments, the proximity sensor comprising one of an acoustic sensor, mechanical sensor, or other contact sensor. In an alternate embodiment, the proximity sensor further includes a bumper coupled to a mechanical sensor or other contact sensor. In some embodiments, the proximity sensor includes an infrared sensor, while in some embodiments, the proximity sensor includes an ultrasonic sensor, and in some embodiments the proximity sensor includes a capacitive sensor.

In some embodiments, the movable backscatter inspection system also includes an indicator for alerting an operator when the predefined separation is detected, the indictor comprising at least one of a visual indicator and an audio indicator.

In some embodiments, the movable backscatter inspection system further includes brakes for slowing or stopping the motion of the base when the predefined separation is detected.

In some embodiments, the movable backscatter inspection system includes a plurality of acoustic sensors.

In another embodiment, a movable backscatter inspection system for interrogating an object includes a movable base; a source of a pencil beam of penetrating radiation, the source having an axis of transmission; a scan head coupled to the base, the scan head comprising at least one detector characterized by an alignment vector, the axis of emission oriented in substantially the same direction as the alignment vector so that the detector is oriented to receive backscatter of the penetrating radiation; and at least one proximity sensor fixed to the scan head, and arranged to detect a first predefined separation between the scan head and the object along a first axis. In yet other embodiments, the movable backscatter inspection system further includes a second proximity detector arranged to detect a second predefined separation between the scan head and the object along a second axis, the second axis not parallel to the first axis.

In still other embodiments, the movable backscatter inspection system includes a third proximity detector arranged to detect a third predefined separation between the scan head and the object along a third axis, the third axis not parallel to the first axis or the second axis, wherein the sensors define a sensing bubble around a portion of the scan head, and in still other embodiments, the three axes are mutually orthogonal.

BRIEF DESCRIPTION OF THE DRAWINGS

The foregoing features of embodiments will be more readily understood by reference to the following detailed description, taken with reference to the accompanying drawings, in which:

FIGS. 5A and 5B schematically illustrate a scan head with bumpers;

DETAILED DESCRIPTION OF SPECIFIC EMBODIMENTS

In accordance with illustrative embodiments, a backscatter inspection system is configured to access confined spaces, and other places that may be difficult or impossible to reach with conventional backscatter inspection systems. To that end, embodiments of a backscatter inspection system include an articulated arm to reach into tight, remote spaces, and proximity sensors to warn an operator when a portion of the system is too close to an object being inspected. Some embodiments include one or more rotating low-power sources of penetrating radiation, and scatter detectors arranged to detect backscatter from the rotating sources.

In addition, some inspection systems may produce digitized data from the detected backscatter radiation. Such data may be used, for example, to produce an image of the object being inspected.

The following definitions may be useful in understanding the various embodiments described herein, and in any claims appended hereto.

A "radiation source" shall refer to a source of a pencil beam of penetrating radiation. An example of such penetrating radiation would be x-rays, and the present invention may be described, herein, in terms of x-rays, but without limiting intent. The pencil beam defines an axis of propagation of the radiation, which may be referred to as a beam axis.

The term "alignment vector," when used with respect to a scatter detector, shall refer to a direction defined by a linear locus of points extending outward from the detector, with respect to which the solid angle subtended by the volume of the detector as seen from an observation point on the locus of points exceeds the solid angle as seen from any other point in a plane, which plane is transverse to the vector at the observation point. Thus, simply put, the alignment vector points in the direction of locations for which the detector is most effective in detecting scatter.

I. Nimbly Positionable Backscatter Inspection System

A mobile backscatter inspection system may encounter objects with irregular shapes. Such objects may present surfaces, contours and spaces that would be difficult or impossible to inspect with a conventional backscatter system. Therefore, some embodiments are nimbly positionable so as to be able to maneuver the system and/or a scan head around obstacles and into hard-to-reach spaces. These systems extend the usefulness of backscatter systems to applications previously unavailable.

Figure 1A:
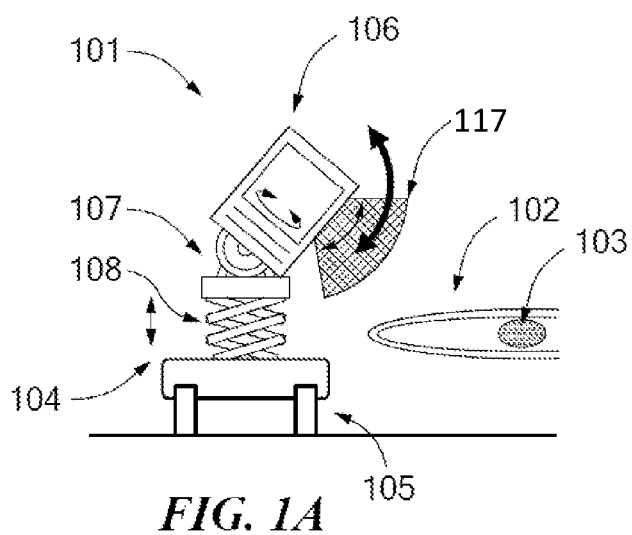
FIGS. 1A-1C schematically illustrate embodiments of a nimbly positionable backscatter inspection system.

FIG. 1A schematically illustrates a nimbly positionable backscatter inspection system 101, in accordance with an embodiment of the present invention, adjacent to an aircraft's wing 102. Because the wing 102 is close to the ground, an attempt to place a conventional backscatter system beneath a central portion of a wing may be impossible given the size of backscatter systems. Likewise, an attempt to place an inspection system above the wing 102 may be impossible given the weight of backscatter systems, and the difficulty in safely lifting and orienting such systems.

The wing 102 also includes an interior space 103 that, for similar reasons, would be difficult or impossible to inspect with a conventional backscatter system. Since spaces within aircraft wings are prime spots to store or smuggle contraband goods, there is a need for a backscatter inspection system with the ability inspect such places.

In contrast to conventional systems, the system 101 is well suited to such tasks. The system contains three main components—base, arm and scan head—that together allow the system 101 to reach and inspect a variety of irregular surfaces and spaces.

A mobile base 104 provides the foundation for the system 101. The mobility of the base allows the system to be easily moved to the object being inspected, or relocated to various positions around the object being inspected. In this embodiment, the base 104 is on wheels 105, but a base could also have tracks or treads, for example.

The base 104 is relatively small for example smaller than a truck or forklift, to enhance its maneuverability. However, the base 104 also has size and weight sufficient to provide a stable platform for the arm and scan head as they extend away from the base. In some embodiments, the base may have a footprint on the ground greater than 30 inches on a side.

The work of illuminating the object and capturing backscatter radiation is done by scan head 106. To inspect an object, the scan head is movable relative to the base 104, and therefore relative to the object being inspected. As such, the system can inspect various portions of the wing 102, for example, without having to position an entire inspection system below or above the wing.

The scan head 106 illuminates the object with a radiation source, and captures backscatter radiation with at least one detector (for example, see FIGS. 5A and 5B). The radiation source produces a pencil beam of penetrating radiation along a transmission axis to illuminate an object being inspected. In some embodiments, the radiation source may move relative the base so as to point or scan the transmission axis in a variety of directions. In this way, it is not necessary to move the entire scan head 106 to inspect a different portion of the object. In FIG. 1A, the fan-shape 117 extending from the scan head 106 is not a physical feature of the scan head; rather is indicates a range scanning allowed by the radiation source. The at least one detector is located in a fixed position relative to the radiation source, but not on the transmission axis, and oriented so as to capture radiation scattered from the object being inspected.

In addition, the scan head 106 may pivot about an axis normal to the arm that supports it, as indicated by the double-headed arrow within the scan head. As such, the system illustrated in FIG. 1A has a number of degrees of flexibility.

To inspect an object, an operator maneuvers the base 105 to the object to be inspected, and extends a scan head 106 from the base via an arm 107. To that end, arm 107 includes a number of segments that facilitate the movement of the scan head 106 in a variety of ways, including elevating the scan head, and extending it laterally away from the base 104. In the embodiment of FIG. 1A, the arm includes a lifting mechanism 108 to elevate the scan head 106 above the base 104 (i.e., vertically with respect to the base 104). This allows the scan head 106 to inspect the wing 102 from above as schematically illustrated in FIG. 1B, without having to position the entire scanning system above the wing 102.

Figure 1B:
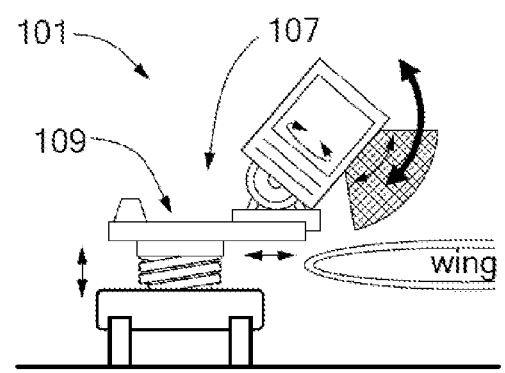

One or more extendable components 109 of the arm 107 further increase the flexibility of the system, as illustrated in FIG. 1B. For example, an arm segment may be a telescoping member, or a scissor-like member. Extensible arm 107 supports scan head 106 so that the scan head can move laterally with respect to the base 104. In some embodiments, the segment of the arm 107 nearest the base may remain stationary as other parts of the arm extend, turn, rotate, or otherwise move or change positions or orientations to reposition the scan head. As such, the arm 107 may extend away from the base 104 to a distance at least as far as the base is wide, and in some embodiments, the length of the arm may be 2, 3 or even more times the width of the base.

Figure 1C:
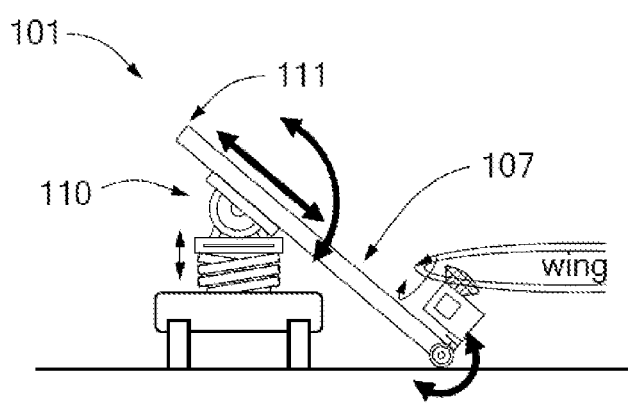

In some embodiments, as schematically illustrated in FIG. 1C for example, the scan head 106 is configured to rotate back towards the extensible arm such that transmission axis of the radiation source is pointing up towards the wing 102. This facilitates inspection of the underside of the wing, or other difficult-to-reach portions of the wing, without having to position an entire backscatter inspection system beneath the wing.

Figure 2:
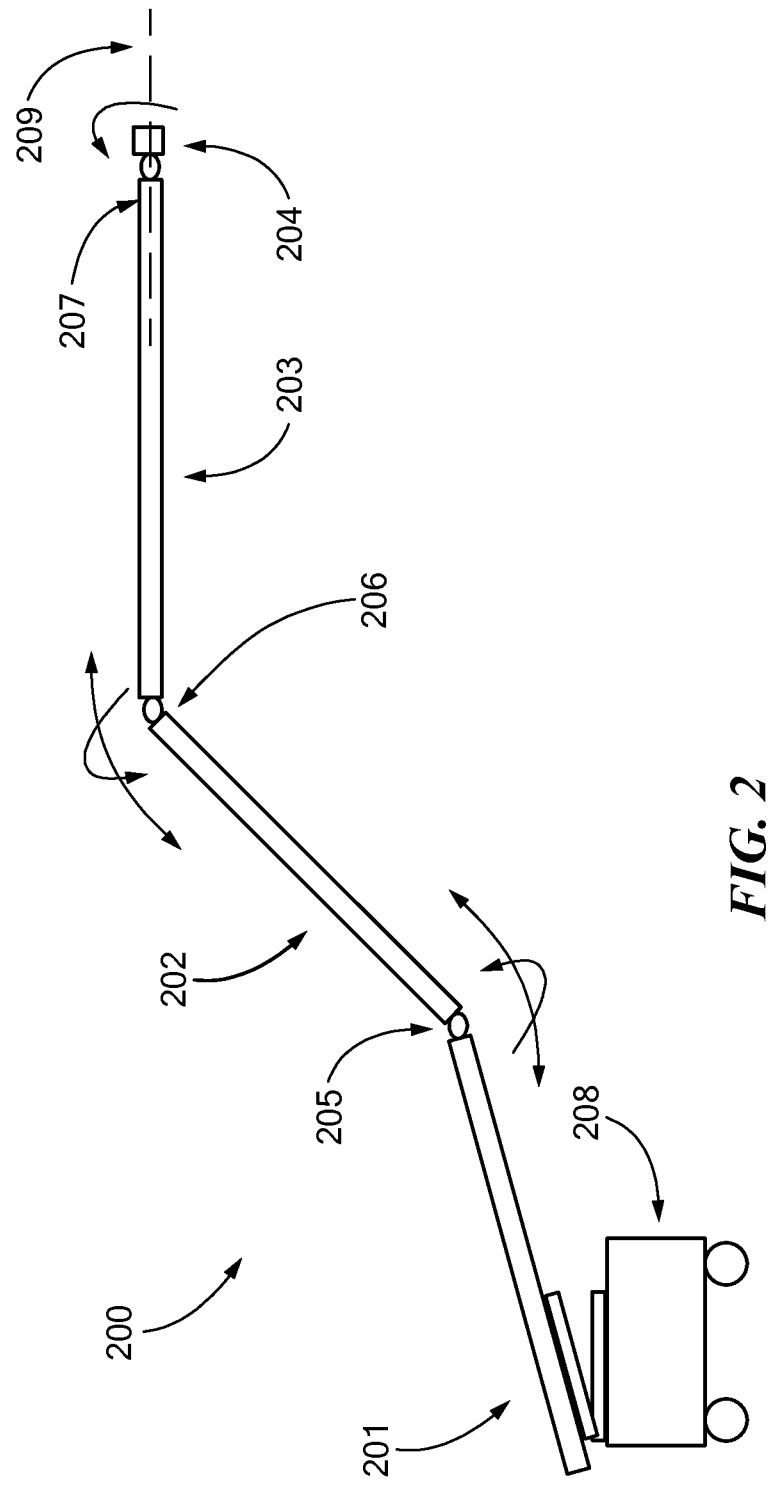
FIG. 2 schematically illustrates a multi-segmented arm.

The arm can have any number of segments, and may be extensible and/or articulated to provide any desired number of degrees of freedom. Another embodiment of a multi-segment arm 200 is schematically illustrated in FIG. 2. Arm 200 has three arm segments (201, 202 and 203), the segments coupled by joints (205 and 206) that allow several degrees of freedom with respect to the others and a base, as indicated by the double-headed arrows near the joints 205, 206 and scan head 204. In addition, one or more of the arm segments may be extendable.

Arm segment 203 is characterized by an axis 209 along its length, and scan head 204 is rotatably coupled to arm segment 203 by movable joint 207 so as to be able to rotate around that axis. As such, the scan head 204 and arm 200 may have seven or more degrees of freedom with respect to a base 208 supporting the arm. The system may thus allow the scan head 204 to be moved in and around object, and even through ports in the object, to maneuver the scan head to a location to be inspected. For example, a system with arm 200 placed outside of a small aircraft could maneuver the scan head through a passenger door or other opening in the fuselage and into the cockpit. The scan head would then be able to rotate about the axis 209 to form a 360 degree image of the interior of the cockpit. Other embodiments may have more or fewer arm segments and moveable joints, and have more or fewer degrees of freedom. For example, some embodiments may include an arm with one end movably coupled to a movable base, and a scan head coupled to the other end of the arm with three degrees of freedom. Such an embodiment would have five degrees of freedom, if moving the base is considered to provide one of those degrees of freedom.

Some embodiments also include an additional movable joint 110 between the lifting mechanism 108 and the first segment 111 of the arm 107, as schematically illustrated in FIG. 1C. The movable joint 110 may tilt the extensible segments of the arm 107 down so that scan head may approach the wing 102 from its underside, or up so that scan head may approach the wing 102 from above.

As illustrated, various embodiments allow the scan head to be moved significant distances from the base, including distances that are greater than the dimensions of the base itself. Extending the scan head will move the center of gravity of the system, but must not be allowed to move the center of gravity beyond the outside edges of the base, to reduce the possibility of tipping. As such, the base should be wide enough so that the center of gravity of the system does not extend beyond the edges of the base. The exact dimensions of the base required to avoid tipping, will depend on the weight and the maximum extension of the arm. For example, in some embodiments, the base is at least 30 inches on an edge, and in some embodiments even greater.

II. Backscatter Inspection System with Collision Avoidance

Some objects to be inspected, such as aircraft for example, have a thin outer skin or are otherwise susceptible to damage. A slight motion, or a miscalculation by a system operator, could cause a base or scan head to contact the object, potentially damaging both the object and the scan head or base. For this reason, some embodiments include sensing and control features to alert the operator, and/or to slow or stop the motion of the system, when a portion of the system is within a defined distance of an object.

Figure 3A:
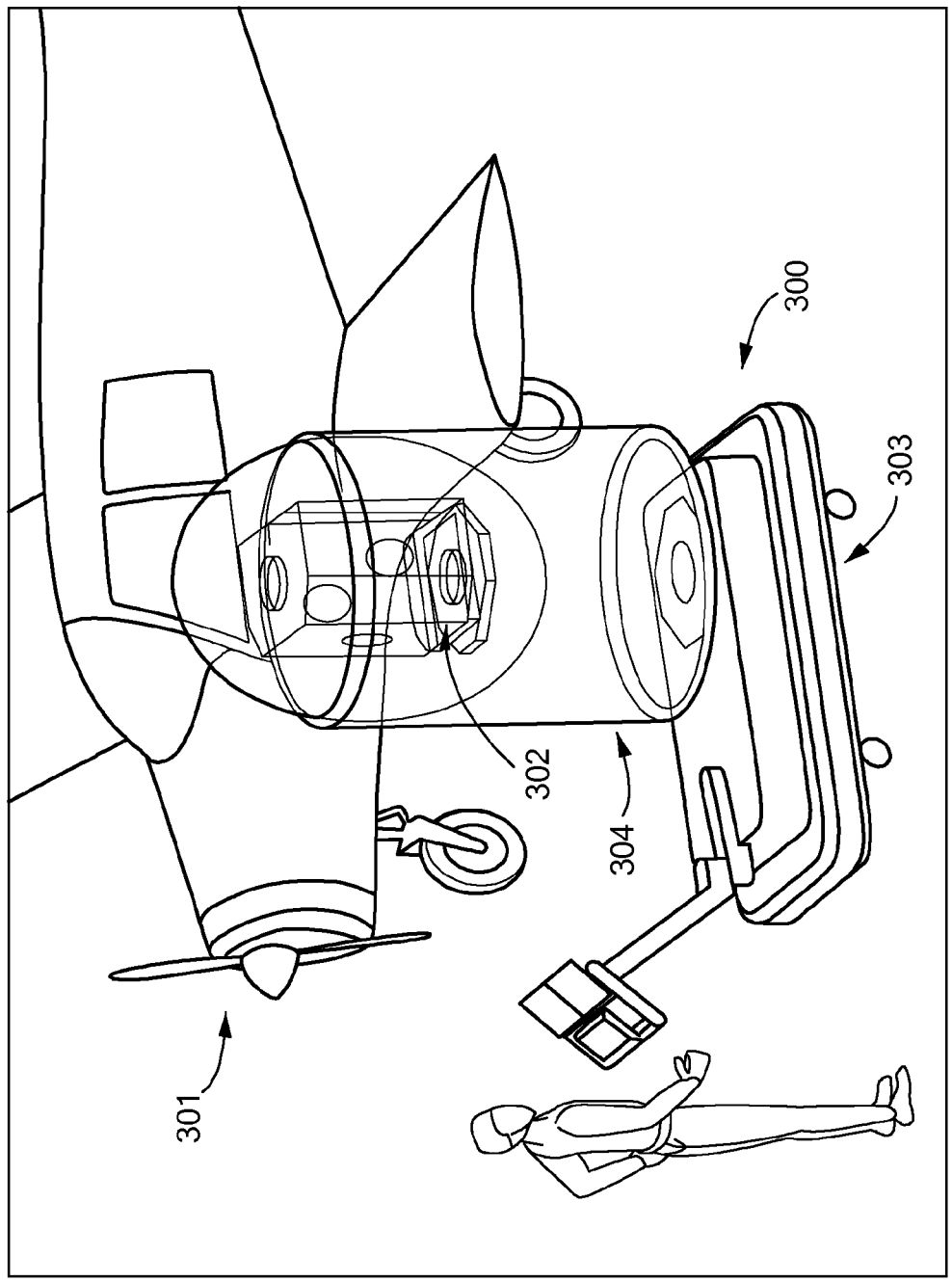
FIG. 3A-3C schematically illustrate embodiments of backscatter inspection systems with collision-avoidance features.

One such embodiment is schematically illustrated in FIG. 3A, in which a backscatter inspection system 300 is adjacent to a small aircraft 301. A number of sensors on the scan head 302, such as sensors 401-406 in FIG. 4, form a sensing perimeter 304, or bubble, around the scan head 302. The sensors detect any portion of the aircraft 301 that breaks the perimeter 304, thus alerting the operator, or even stopping the motion of the scan head 302 or base 303. As such, the system 300 has a collision avoidance subsystem. Some embodiments similarly include sensors on and around the base 303, to prevent the base from contacting the object being inspected, or other objects.

Figure 4:
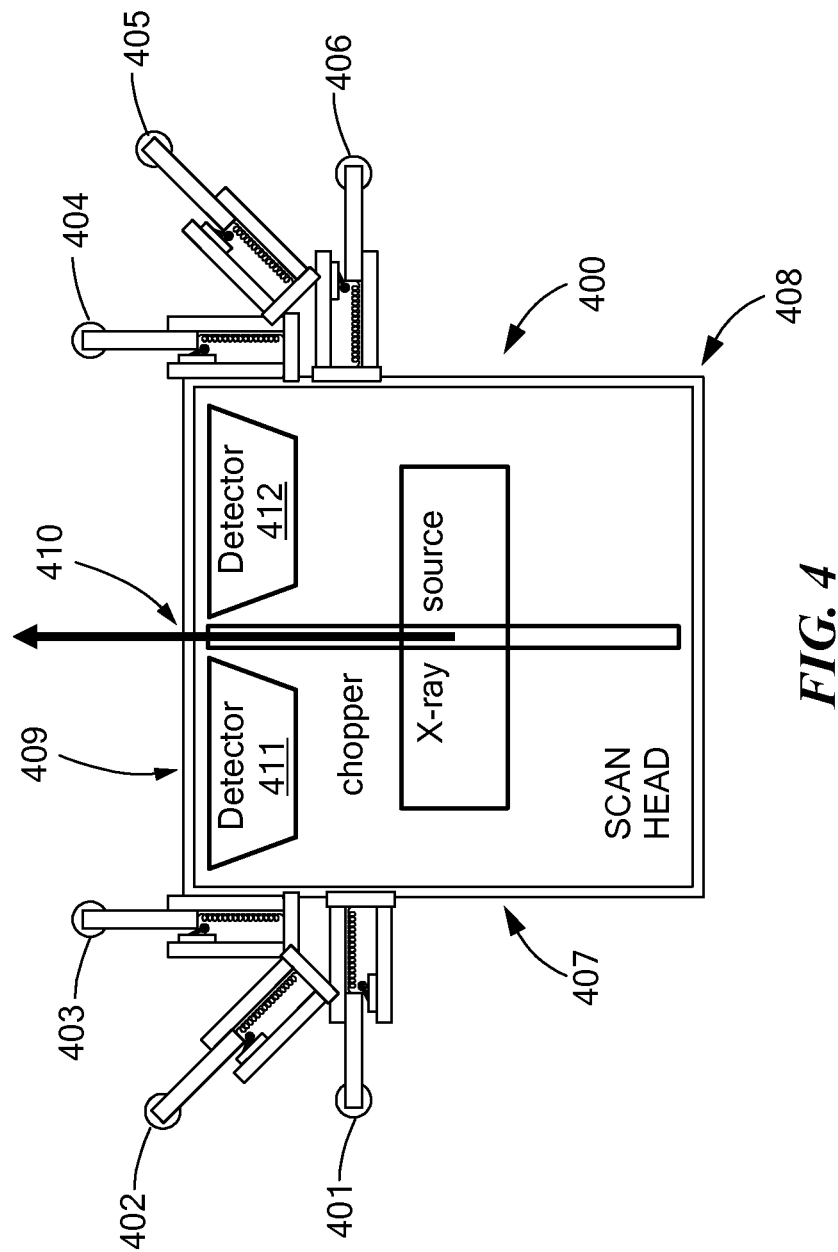
FIG. 4 schematically illustrates a scan head with a number of contact sensors.

The scan head 400 of FIG. 4 has contact sensors 401-406 forming a sensing perimeter on three sides. Each of the sensors 401-406 has a direction in which it can sense contact with an object, such as the skin of an aircraft for example, and so numerous sensors provide numerous opportunities for detection. That direction may be referred to as an axis of sensitivity.

Some sensors, such as 403 and 404, point in the same direction, but at different locations on the scan head 400. Such sensors may provide redundant sensing, or may allow the system to sense its angle of approach to an object. For example, if the scan head 400 approaches an object at an angle, sensor 403 might detect contact before sensor 404. As such, a system operator may change the trajectory of the moving scan head 400 to maintain the separation between the scan head 400 and the object as detected by sensor 403, but continue to move closer until, for example, sensor 404 also encounters the object. In this way, the scan head 400 can be maneuvered close to, and indeed parallel to, a surface being inspected.

Other sensors point in various directions to extend and shape the sensing perimeter. For example, sensors 402 and 405 are at an angle to sensor 403 and 404. Some sensors, such as 401 and 406 may even point in directions 180 degrees from each other, in this case to protect the sides 407 and 408 of the scan head 400. As such, a number of sensors can be angled with respect to one another such that none of the sensors has an axis of sensitivity that is parallel to the axes of sensitivity of the others. Indeed, some embodiments may include three sensors with mutually orthogonal axes.

Figure 3B:
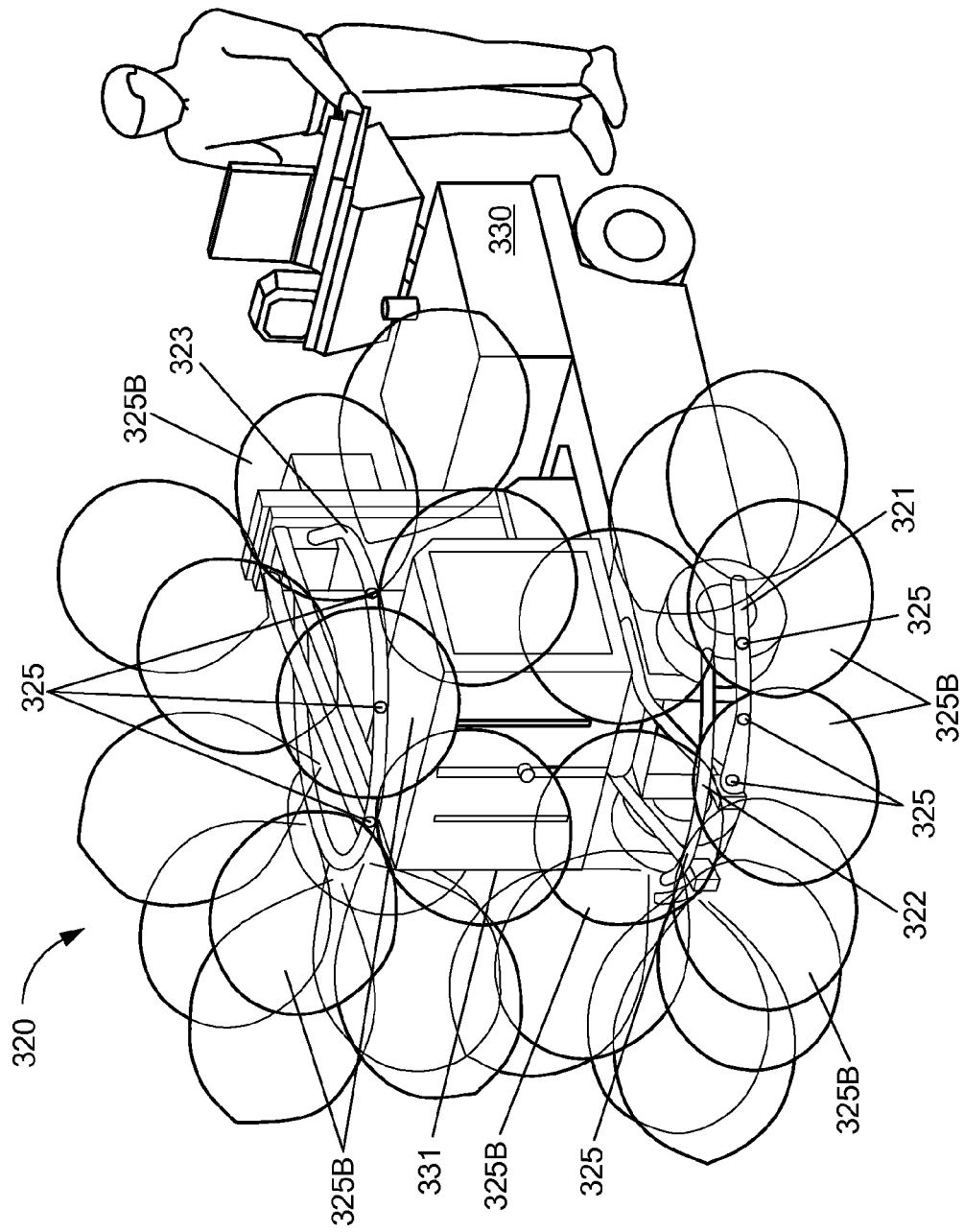

Another embodiment of a system 320 having sensing and control features to alert the operator, and/or to slow or stop the motion of the system, when a portion of the system is within a defined distance of an object is schematically illustrated in FIG. 3B. This embodiment includes several arcs 321, 322 and 323 of acoustic sensors that act as proximity sensors. In some embodiments, the acoustic sensors 325 on the arcs 321, 322 and 323 may be of the type commonly used as backup sensors in the automotive industry, for example, while in other embodiments the sensors could detect other forms of energy, such as infrared or electromagnetic energy, such sensor operating similarly to the acoustic sensors described herein, but using different forms of energy. In some embodiments, each acoustic sensor 325 may be a transducer that can both transmit and receive an echo from an acoustic signal. A processor, such as a microprocessor or timer may be employed to determine the distance between a sensor 325 and an object by determining the time between the transmission of an acoustic signal and the receipt of an echo (if any) of that signal. To that end, each sensor 325 may modulate a its transmitted signal with an identifiable modulation, such as a binary code for example, so that the transmitting sensor can distinguish an echo of its transmitted signal from the echoes of signals transmitted from other sensors 325.

Each acoustic sensor may be described as establishing a zone of sensitivity in the space near the sensor. In FIG. 3B, such zones of sensitivity are schematically illustrated as bubbles 325B. An object within the zone of sensitivity (e.g., within a bubble) will produce an echo from the associated sensor to indicate the proximity of the sensor (and sensor arc) to the object. In other words, objects within the zone of sensitivity may be identified as being near the sensor. Such an indication may be processed and presented to the user as an alert as to the proximity of the object, or used in other ways described in connection with FIG. 3A.

Figure 3C:
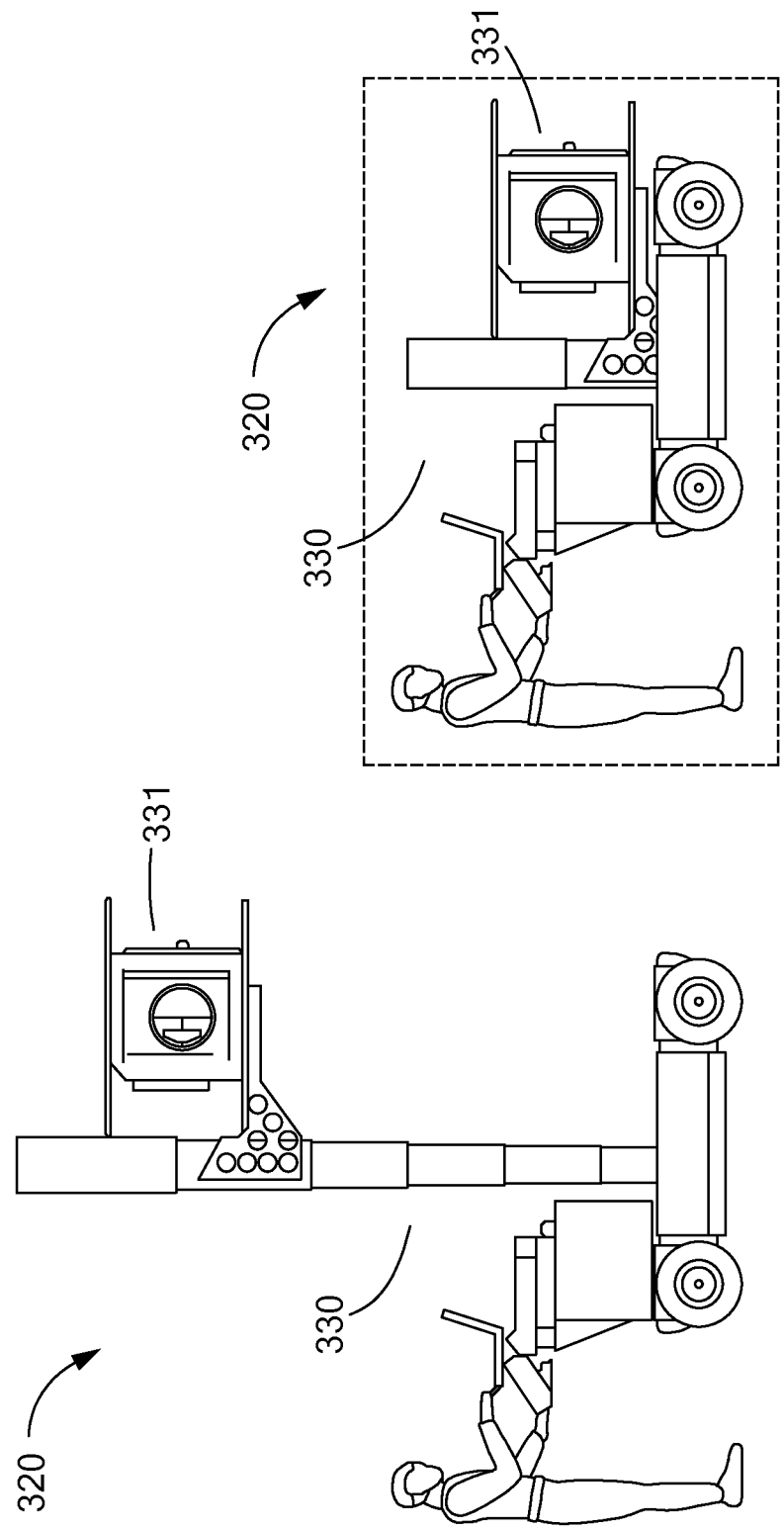

In FIG. 3A, the lowest arc 321 is near the bottom of the backscatter inspection system 330. However, the scanner head 331 may be raised, as schematically illustrated in FIG. 3C. In some embodiments, one or more of the sensor arcs 321, 322, 333 remain near the bottom (e.g., near ground level), while one or more of the other sensor arcs move with the scanner head 331. In this way, one arc (e.g., arc 321) remains near the ground to detect objects near ground level, while at least one other arc (e.g., arc 323) travels with the scanner head 331 to detect objects near the scanner head 331.

In some embodiments, the sensors 325 may be the type of sensors used in the automotive industry. Such sensors typically are provided in sets of four (4) sensors, in which each sensor in the set is configured to transmit a unique signal so as to avoid interfering with the operation of other sensors in the set. In other words, no two sensors within a set employ the same modulation, and therefore no two sensors in the set are alike. For example, the sensors of the set may be designated as S1, S2, S3 and S4.

If a sensor arc, or a set of sensor arcs includes more than one such set, some embodiments may arrange the sensors so as to minimize or avoid any interference between like sensors. For example, if each arc 321, 322, 324 has a set of four sensors, the sensors might be arranged on the arcs as follows:

| Arc 321: | S1 | S2 | S3 | S4 |
| Arc 322: | S3 | S4 | S1 | S2 |
| Arc 323: | S1 | S2 | S3 | S4 |

In this way, no sensor on one arc is immediately adjacent to a like sensor on another arc. In some embodiments, a given sensor arc may include more than one set of sensors. In such embodiments, the sets should be arranged so that no sensor on an arc is adjacent to a like sensor on that arc, and no sensor on one arc is immediately adjacent to a like sensor on another arc. In addition, or in the alternative, in some embodiments, the sensors are separated not only by their distance from other sensors on the same arc, and not only by their distance from sensors on other arcs, but also because the arcs have a curvature, so that the bubbles around the various sensors are oriented in different directions.

Some embodiments may include two or more sensors to detect various separation distances between a scan head and an object being inspected. For example, a first sensor may detect a separation of 20 centimeters in a given direction, and a second sensor may detect a separation of only 15 centimeters in that same direction. If the first sensor is triggered, the system may alert the operator via a light, or an audible alarm for example, and/or cause an onboard control system to slow the motion of the base or the scan head. If the second sensor is triggered, the control system may promptly stop the motion of the scan head and/or the base.

The front 409 of the scan head 400 may be particularly challenging to protect, because sensors cannot be placed in front of the source 410 or the detectors 411 and 412. In other words, a sensor should not be located in such a way that it blocks transmission of radiation by the source 410, or blocks backscattered radiation from reaching the detectors 411 and 412.

To meet that challenge, some embodiments include bumpers 501, 502 and 503 coupled to the sensors, as schematically illustrated in FIGS. 5A and 5B. The bumpers effectively extend the bubble or perimeter to the front face 507 of the scan head. In the embodiment illustrated in FIG. 5B, bumpers 504A-504D form a frame 504 in adjacent to the face 507. An object, such as a portion of an aircraft for example, that contacts a bumper will activate at least one of the sensors 505 or 506. At the same time the bumpers do not block the source 410 or the detectors 508, 509. In addition, the bumpers may be constructed from materials that are transparent to the radiation, so further reduce the potential for interference.

Similar bumpers 501, 503 may be employed on the sides 510 and 511 of the scan head 500. Here, there is no risk of blocking desirable radiation, but such bumpers are valuable because they can easily extend the sensing perimeter without having to add additional sensors. For example, in contrast to the scan head 400 of FIG. 4, the sensing perimeter of scan head 500 extends past sensor 512 and further towards the back side 513 of the scan head 500. Similarly, the bumpers will engage an approaching object near the corner 514 (i.e., the region between sensors 506 and 515) without requiring an additional sensor, and at a further distance than might be detected by sensors 515 and 506 alone.

In some embodiments, the bumpers may allow the sensors to work together to provide information about where the scan head is closest to the object. For example, if sensor 505 is triggered but sensor 506 is not, then the system may infer that the object is closest to sensor 505. However, if both sensor 505 and sensor 506 are triggered, the system may infer that the object is near the center of bumper 502.

Although the sensors in the preceding embodiments have been described as contact sensors, other types of sensors may be used in alternate embodiments. For example, various applications might benefit from the use of capacitive sensors, infrared sensors, or ultrasonic or other acoustic sensors, electromagnetic sensors, or various types of mechanical sensors, to name but a few.

However, contact sensors are versatile, and should not be overlooked. For example, some contact sensors are well suited for use with bumpers, as described above. Also, some contact sensors may be able to detect more than one separation distance, or even report separation distance in many fine increments.

Figure 6:
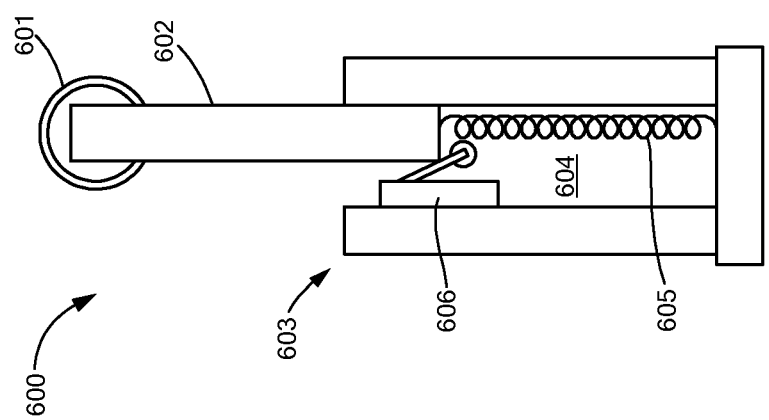
FIG. 6 schematically illustrates a contact sensor.

One embodiment of a simple mechanical contact sensor 600 is schematically illustrated in FIG. 6. In this embodiment, the mechanical sensor 600 includes a tip 601, a plunger 602, and a housing 603. When the tip 601 contacts an object, the plunger 602 recedes into a cavity 604 in the housing 603. This prevents the tip 601 from puncturing, scratching or otherwise damaging the surface or the object. In fact, the force applied to the object may be controlled by the spring 605. The spring 605 serves to keep the plunger 602 fully extended when not in contact with an object, but otherwise allows the plunger 602 to recede into the cavity 604.

As the plunger 602 recedes into the cavity 604, its travel trips a microswitch 606, sending a signal from the switch to a control system. The control system, which may include a microprocessor programmed with specific software, or other processing circuitry, will then know the distance between the scan head and the object into which the scan head has come into contact and may react accordingly. For example, the control system may react by applying brakes to the wheels of the base to stop or slow the base, to prevent the scan head from moving any closer to the object. Similarly, the control system may stop or slow the movement of the scan head. Of course, the control system may also alert the operator by means of an audible or visual signal.

Although contact sensor 600 includes a microswitch 606 in this embodiment, a variety of other sensors could be used to sense the motion of the plunger, including optical or magnetic sensors for example.

In addition, a number of switches (or other suitable detectors) may be placed various depths within the cavity 604, each detecting a successively greater penetration of the plunger 602. To that end, and/or to allow the plunger additional range to retract when in contact with an object, the depth of the cavity 604 may allow the plunger to penetrate the cavity for an additional distance after the plunger triggers the microswitch. Indeed, in some embodiments that additional distance may exceed the distance initially required for the plunger to trip the microswitch in the first place.

III. Backscatter X-Ray Inspection System for Confined Spaces

The inspection of some objects or spaces may benefit from placing the backscatter inspection system within the object or space. For example, the interior of a passenger aircraft may limit the dimensions of a system used with the aircraft, and objects such as seats, walls and overhead bins within the aircraft may limit or impede the extension or manipulation of arms. Similarly, a cave harboring improvised explosive devices may present tight spaces and irregular contours, and an otherwise large room in a building with sheetrock walls may include tight spaces like corners, or may include furniture or other structures that may limit or impede the extension or manipulation of arms.

The inspection of some objects or spaces may benefit from the application of backscatter inspection system with relatively small components capable of reaching tight spaces. For example, some objects may present external contours that may limit or impede the extension or manipulation of arms, such as a tight space between the wing and fuselage of an aircraft, or the crevice between the surface of a wing or fuselage, and an engine nacelle, to name but a few.

To those ends, some embodiments are compact and do not depend on extendable arms, or require that their detectors be as close as possible to the surface being inspected. Illustrative embodiments described herein involve the inspection of a commercial jetliner from within the fuselage of that jetliner, but it is understood that embodiments could be used to inspect the inside or outside of other locations, such as building, ground vehicles, and caves, for example.

Figure 7:
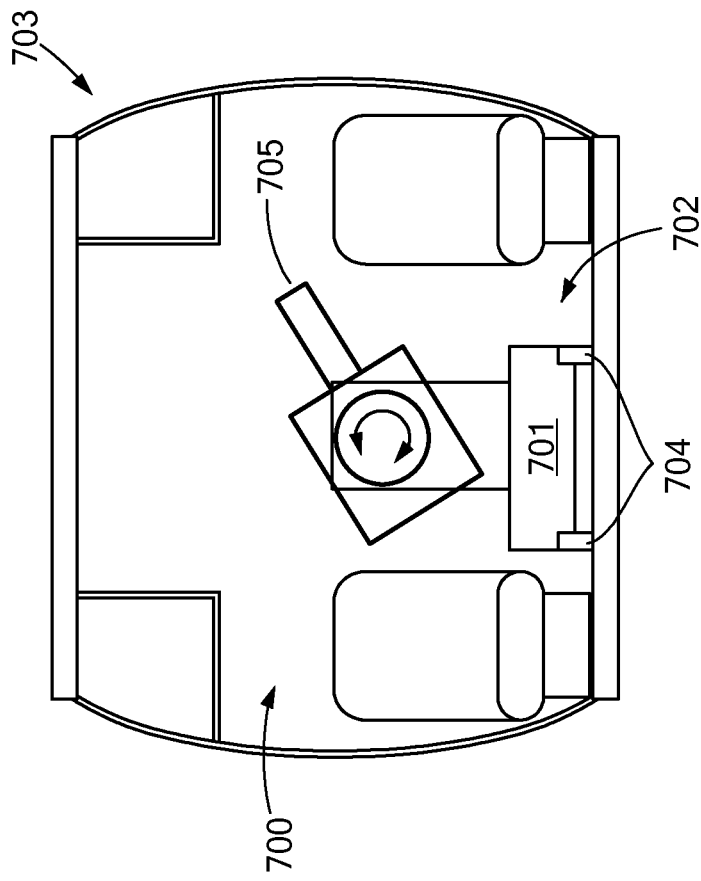
FIG. 7 schematically illustrates a backscatter inspection system within an aircraft fuselage.

An embodiment of such a backscatter inspection system 700 is schematically illustrated in FIG. 7, in which a movable base 701 is shown in the aisle 702 of a commercial jetliner 703, or other aircraft. The elements of the system 700 are sized and arranged so that the system 700 will fit and operate within the fuselage of the aircraft 703.

Specifically, the dimensions of the base 701 are limited to allow the base to fit in the aisle 702. Further, the base 701 is movable so that it may scan the length of the aircraft's fuselage by moving down the aisle 702. To that end, the base may have wheels 704 or castors, for example.

Figure 8:
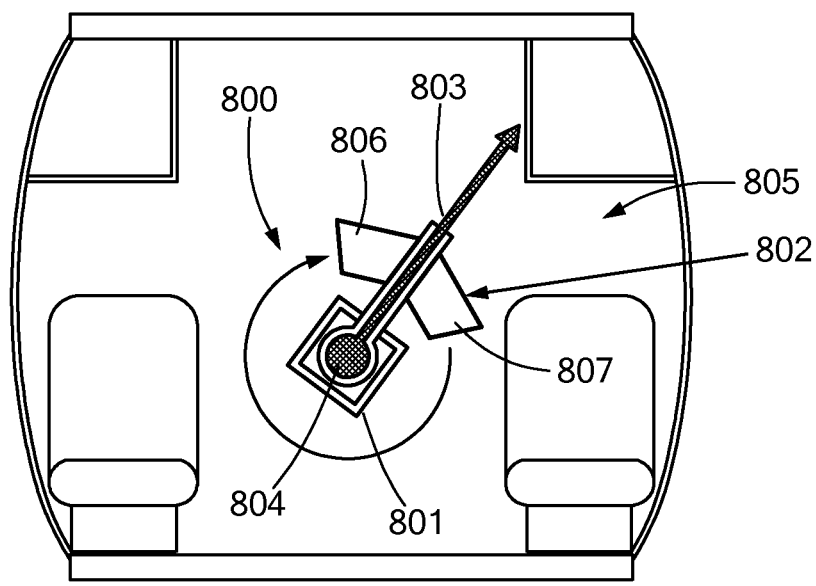
FIG. 8 schematically illustrates a rotatable scanning platform.

The system 700 illuminates portions of the interior of the aircraft 703 by rotating a radiation source 705 in a vertical plane (i.e., vertical with respect to the floor), and detects backscattered radiation with one or more detectors (for example, as shown in FIG. 8). The vertical plane may, or may not, be perpendicular to the long axis of the aisle 702.

In some embodiments 800, as schematically illustrated in FIG. 8 for example, a scanning platform 801 is rotatably coupled to the base (for example, a base as shown in FIG. 7), and includes a source 802 capable of producing a pencil beam of penetrating radiation from an emission point 803. Here, the emission point is a region of finite area where the beam of penetrating radiation emerges from they radiation source 802. The pencil beam defines the transmission axis that emanates from the emission point and that is normal to the axis 804 about which the scanning platform 801 rotates. In operation, the emission point 803 and beam of penetrating radiation may sweep an arc or circle about the axis of rotation 804, and thereby illuminate a portion or all of the surrounding aircraft 805.

Inspecting the interior features of an aircraft may benefit from limits on the energy output of the radiation source. It known that some radiation, such as X-rays, maybe hazardous. Generally, it is beneficial, and safer, to use radiation at or near the lowest energy level sufficient for a given inspection. A limit on the energy output of the radiation source may be dictated by the surface or material to be inspected. For example, it is known in the art that for a given material, there is an energy at which Compton scattering begins to dominate photoelectric absorption. That point is generally a function of the atomic number (Z) of the material. As such, the choice of energy output may be a function not only of the material to be inspected (and more particularly, to the atomic weight of that material), but also of the type of scattering the system is designed to detect (e.g., incident rays subject to Compton scattering, or electrons emitted due to the photoelectric effect). In some embodiments illustrated herein, the material will include aluminum (with an atomic number Z=13), so a system designed to detect electrons emitted due to the photoelectric effect may be limited to energies at or about 70 keV. However, other systems have greater or lesser energies, and so discussions of systems operating at or below 70 keV are for illustrative purposes only, and do not limit the scope of the disclosure herein. Similarly, some embodiments disclosed herein include reference to the energy spectrum of the penetrating radiation. However, in some embodiments, the energy source may be a monoenergetic source, such as an isotope source for example. As such, descriptions of the energy spectrum of the penetrating radiation do not limit all embodiments to sources that are not monoenergetic.

Use of a relatively high-energy radiation is unavoidable when the system needs to inspect interior portions of fuselage walls, for example, since the radiating must be energetic enough to penetrate to such interior portions and produce detectable backscatter. On the other hand, inspecting the interior of an aircraft, including its contents (e.g., plastic panels, foam and cloth seats, etc), may be successfully performed using relatively lower-energy radiation. Specifically, the radiation need only be energetic enough to penetrate such materials. For example, in some embodiments inspecting the interior of an aircraft, the energy level of the radiation is insufficient to penetrate the walls of fuselage (e.g., to avoid getting backscatter from objects within or beyond to the walls, or to avoid transmitting radiation beyond the interior of the aircraft).

Therefore, some embodiments operate at a low energy, such as an energy at or below 70 keV. The radiation may be such that the photoelectric attenuation of the penetrating radiation by the metal enclosure of an aircraft exceeds the scattering of the penetrating radiation by the metal enclosure over the entire energy spectrum of the penetrating radiation. Such low energy (e.g., 70 keV or less) is nevertheless sufficient to inspect interior spaces. As an additional benefit, such a power source avoids the weight of a more powerful system.

To detect backscattered radiation, the system 800 includes a pair of scatter detectors 806, 807 that rotate with the source 802. Each scatter detector 806, 807 has an alignment vector that may or may not be parallel to the beam axis, but which extends in the same general direction as the beam axis so that the detectors 806, 807 are always positioned to encounter at least a portion of any backscattered radiation as they rotate with the source 802.

The detectors 806, 807 in the embodiment of FIG. 8 are not immediately adjacent to the emission point 803. As a consequence, the detectors 806, 807 are not as close the a given point of backscatter as they would be had they been positioned at or near the emission point 803. Some authors (for example, see U.S. Pat. No. 7,623,626 to Safai et al.) believe and advocate that the detectors should be positioned near the point of backscatter as possible, on the theory that such proximity to the backscatter point will maximize the flux of radiation into the detector, improve resolution and prevent distortion, among other things. However, such an approach also means that the combined size of the emission point and the detectors is larger than the size of the emission point alone, with the consequence that the ability to move the emission point close to a surface of the object being scanned may be limited.

The system 800 in this embodiment allows inspection of an object without having to position the detectors near the emission point. The inventors have recognized that the flux at the detectors is a function of the solid angle of the detectors as seen from the point of backscatter, rather than only the immediate proximity of the detectors to that point. In other words, the same amount of backscattered radiation may be detected by larger detectors placed further from the point of backscatter as by smaller detectors placed close to that point.

As such, with detectors mounted away from the emission point, the area of the system near the emission point may be smaller, and therefore more maneuverable and dexterous. Also, placing the detectors nearer the axis of rotation, rather than near the emission point, produces a smaller moment about that axis as the detectors rotate about that axis, allowing greater control of such rotation and finer positioning of the detectors and radiation source. In various embodiments, the detectors may be located at the axis of rotation, or at any point along between that axis and the emission point. In some embodiments, detectors may be located such that the axis of rotation is between the detectors and the emission point.

Figure 9:
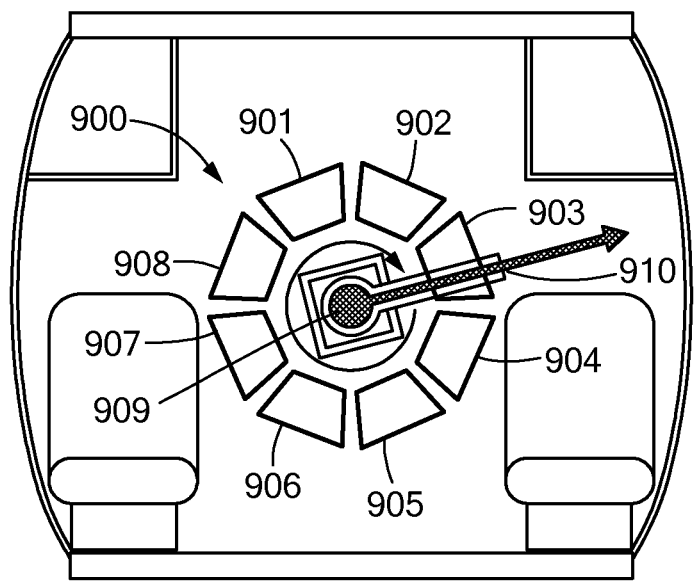
FIG. 9 schematically illustrates a backscatter inspection system with a number of fixed detectors.

Alternate embodiments include detectors that do not rotate with the emission point. The embodiment 900 of FIG. 9 includes a number of detectors 901-908 fixed to the base (not shown) and forming a perimeter around the axis of rotation 909. As such, there is always at least one detector oriented to detect backscatter radiation, irrespective of the position of the emission point 910. A controller, such as a programmed microprocessor or other circuit, may monitor the location of the source 909 with respect to the detectors 901-908, to determine which detector or detectors are best positioned to receive backscattered radiation from that source. The controller may then selectively process data from those detectors. Stated alternately, the controller may selectively activate those detectors, where activating a detector means to process its data, and does not imply that the detector is turned off or otherwise disabled.

Yet other embodiments include more than one radiation source, or at least more than one emission point, to provide a corresponding number of pencil beams of penetrating radiation from a corresponding number of emission points. Such embodiments may be able to deliver more energy to the object being inspected to produce a quicker or more detailed scan.

Figure 10:
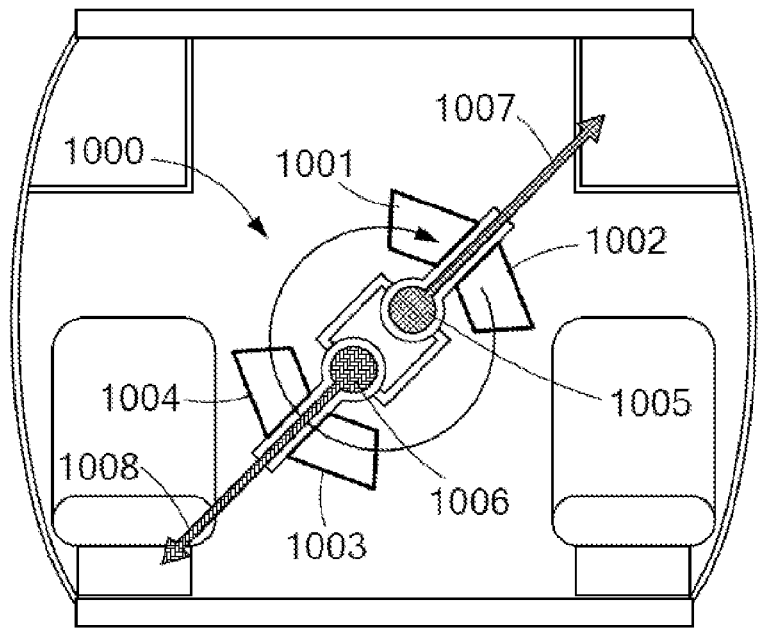
FIG. 10 schematically illustrates a multiple-source backscatter inspection system with rotating detectors.

One such embodiment 1000 is schematically illustrated in FIG. 10, in which two sets of detectors (1001 and 1002; 1003 and 1004) correspond to two radiation sources 1005 and 1006, each with an energy not above 70 keV. Other embodiments may have an energy at or above 70 keV, however, depending on the needs of the intended application of the system.

Each radiation source 1005 and 1006 produces a beam of penetrating radiation along a beam axes 1007 and 1008 respectively, and the beam axes 1007 and 1008 are diametrically opposed. Backscattered radiation from each emission point is then correlated to the detectors associated with each emission point. As such, a 360 degree scan within a vertical plane could be produced with only one half of a rotation about the axis.

Figure 11:
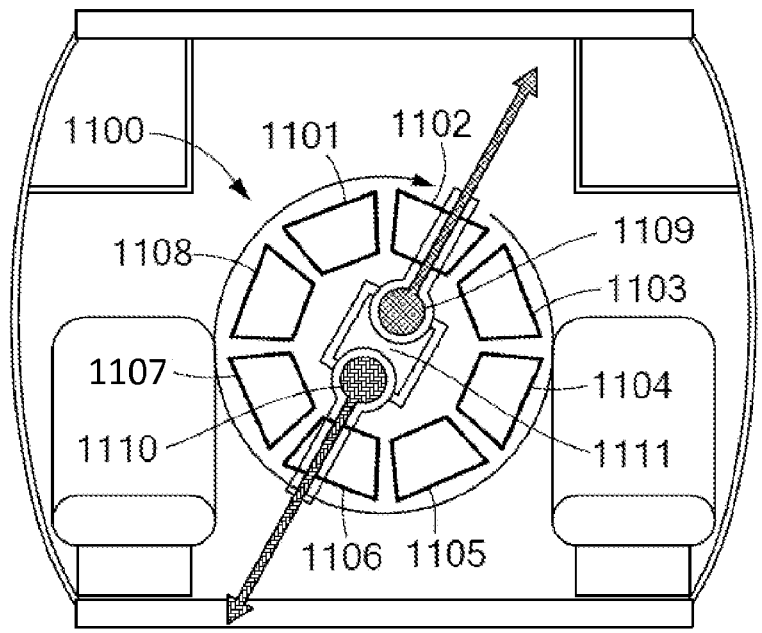
FIG. 11 schematically illustrates a multiple-source backscatter inspection system with fixed detectors.

Yet another embodiment of a multiple-source system is schematically illustrated in FIG. 11, in which a number of detectors 1101-1108 form a perimeter around, but do not rotate with the sources 1109 and 1110 about the axis 1111. In operation, the system 1100 will associate a subset of the detectors 1101-1108 with each source 1109 and 1110, so as to correlate detected backscatter radiation with its source.

For example, a controller associated with the system of FIG. 11 may monitor the location of the two sources, 1109 and 1110, relative to the numerous detectors 1101-1108, and process the detectors' output by dynamically associating subsets of the detectors 1101-1108 with the sources 1109-1110.

For example, when the sources 1109 and 1110 are in the positions illustrated in FIG. 11, the backscatter radiation detected by detectors 1101-1103 is most likely to have originated at source 1109 (and backscattered from another point in the aircraft). Therefore, the controller may associate data from those detectors with source 1109, and process that data accordingly. In contrast, radiation detected by detectors 1105-1107 is less likely to have come from source 1109, and is therefore not associated with that source. Indeed, radiation detected by detectors 1105-1107 is more likely to have originated at source 1110, and is therefore associated with that source and processed accordingly. In other words, data from the various detectors is selectively processed (or the detectors are selectively activated) to correlate the data with the source from which the radiation most likely originated.

Radiation detected by detectors 1104 and 1108, on the other hand, is equally as likely to have originated from either of the source, or even from somewhere else. As such, data from those sensors cannot as reliably be associated with one of the sources as data from the other detectors, and may be discarded.

In contrast, by the time sources 1109 and 1110 rotate 180 degrees they will have exchanged positions. As such, detectors 1101-1103 will then be associated with source 1110, and detectors 1105-1107 will be associated with detector 1109. At various positions in between, detectors 1104 and 1108 will be associated with one detector or another, while the remaining detectors will, from time to time, be in-between the two sources such that their output is not used.

Various embodiments may implement other features. In some multiple-source embodiments, each source may have different energies. Such a system could scan each point on object twice—once with each energy—to produce an image from a combination of the individually detected backscatter images.

Some embodiments may also include one or more distance detectors to ascertain the distance between the system, or a part of the system (e.g., an emission point or a detector), from a surface of the object being inspected. For example, a laser range finder may be mounted to measure that distance along the beam axis of a beam of penetrating radiation. With that information, the system may build a distance map associated with every pixel in a backscatter image. That data, in turn, could be used to remove distortions from the backscatter image (possibly allowing for dimensional reconstruction). Also, for a highly reflective object behind a surface of an obscurant, distance and signal level data could be correlated to estimate the mass (for an assumed Z) of the object. Alternately, if the obscurant can be assumed to be relatively thin and low-Z (as is the case with interior wall panels of an aircraft, for example) a dual energy backscatter system might be used to estimate the Z of any object of interest. This information could then be used in conjunction with distance data and signal level to estimate the mass of the object.

A variety of other embodiments may be described. For example, in a first embodiment there is provided a nimbly positionable backscatter inspection system. The system has an arm coupled to the base. The arm has a first segment, a second segment, and a third segment, as well as a first movable joint coupling the first segment to the second segment, and a second movable joint coupling the second segment to the third segment. A scan head is coupled to the third segment, and includes a source of penetrating radiation for generating a pencil beam of penetrating radiation, the pencil beam characterized by a beam axis, and a primary detector configured to detect scattered penetrating radiation. The scan head is movable in at least 3 to 7 degrees of freedom with respect to the base, and the system is capable of capturing backscatter radiation in a plurality of orientations by moving the scan head while the first segment remains stationary with respect to the base.

In some embodiments, at least one of the first and second arm segments is extendable, and may be a telescoping member. In other embodiments, both the first and second segments are extendable, and may be a telescoping member.

In some embodiments, the third arm segment has an axis along its length, and scan head is rotatable around the axis.

In some embodiments, the mass of the base is sufficient to prevent the base from tipping when the arm is fully extended parallel to the ground, and in some embodiments the base is at least 30 inches wide and 30 inches deep.

The scan head in some embodiments is configured to be contained within an object being inspected.

A method of capturing a backscatter image derived by irradiating a surface that is interior to an object includes the steps of positioning a backscatter inspection system adjacent to the object, wherein the backscatter inspection system has a base, and an extendable arm secured to the base, the arm having at least two segments coupled by a movable joint, and a scan head at a distal end of the arm. The method also includes manipulating the arm to extend from the base through a portal in the object to a volume interior to the object, and irradiating the surface interior to the object with a pencil beam of penetrating radiation. The method then includes a step of receiving backscatter radiation at the scan head, and then processing the backscatter radiation to form an image of a portion of an interior volume of the object. Another embodiment includes manipulating the scan head to sequentially orient the scan head in a plurality of orientations within the volume interior to the object.

A movable backscatter inspection system for interrogating an object includes a source of a pencil beam of penetrating radiation, the source having an axis of transmission (which may be referred to as an axis of emission) and coupled to a base. The system also includes a scan head coupled to the base, the scan head having at least one detector at a location not on the axis of transmission and oriented to receive penetrating radiation scattered by the object, as well; as at least one proximity sensor coupled to the base, and arranged to detect a first predefined separation between the location and the object.

The proximity sensor in some embodiments includes a plunger, and in some embodiments the plunger has a range of travel including a first portion between its fully extended position and a trigger point, and a second portion after the trigger point. In some embodiments, the second portion exceeds the first portion. Plungers in some embodiments further include a bumper coupled to the plunger.

The proximity sensor in some embodiments is an infrared sensor, while in other embodiments the proximity sensor is an ultrasonic sensor, and in yet other embodiments the proximity sensor is a capacitive sensor.

Some embodiments include an indicator for alerting an operator when the first predefined separation is detected, the indictor comprising at least one of a visual indicator and an audio indicator.

Some embodiments include a secondary proximity detector arranged to detect a second predefined separation between the location and the object, the second predefined separation being less than the first predefined separation. Alternate embodiments include an indicator for alerting an operator when one of the first predefined separation or second predefined separation is detected, the indicator comprising at least one of a visual indicator and an audio indicator, and some embodiments include brakes for slowing the motion of the base when the first predefined separation is detected, and/or stopping the motion of the base when the second predefined separation is detected. Some embodiments include an indicator for alerting an operator when the first predefined separation is detected, and brakes for slowing the motion of the base when the second predefined separation is detected.

A movable backscatter inspection system for interrogating an object, the detector including a movable base; a source of a pencil beam of penetrating radiation, the source having an axis of transmission; a scan head coupled to the base, the scan head comprising at least one detector characterized by an alignment vector, the axis of transmission (which may be referred to as the axis of emission) oriented in substantially the same direction as the alignment vector so that the detector is oriented to receive backscatter of the penetrating radiation; and at least one proximity sensor fixed to the scan head, and arranged to detect a first predefined separation between the scan head and the object along a first axis.

Alternate embodiments include a second proximity detector arranged to detect a second predefined separation between the scan head and the object along a second axis, the second axis not parallel to the first axis. Alternate embodiments include a third proximity detector arranged to detect a third predefined separation between the scan head and the object along a third axis, the third axis not parallel to the first axis or the second axis, wherein the sensors define a sensing bubble around a portion of the scan head, and in some embodiments the three axes are mutually orthogonal.

Some embodiments include a second proximity detector arranged to detect a second predefined separation between the scan head and the object along a second axis, the second parallel to the first axis. In alternate embodiments, each of the first and second proximity sensors has a direction of sensitivity, and the direction of sensitivity of the second proximity sensor is 180 degrees from the direction of sensitivity of the first proximity sensor.

A movable backscatter inspection system for inspecting contents of a space confined by an enclosure (which may be confined by a metal enclosure) includes a scanning platform rotatably coupled to a movable base, the scanning platform having an axis of rotation; a source of radiation characterized by an energy spectrum, the source coupled to the scanning platform and arranged to transmit a pencil beam of penetrating radiation from an emission point, the beam having a beam axis projecting outward from the axis of rotation, photoelectric attenuation of the penetrating radiation by the metal enclosure exceeding scattering of the penetrating radiation by the metal enclosure over the entire energy spectrum of the penetrating radiation; and a first detector characterized by a detector volume, the first detector coupled to the scanning platform at a location such that the entire detector volume is closer to the axis of rotation of the scanning platform than the emission point is to the axis of rotation of the scanning platform, whereby the first detector rotates with the radiation source. In alternate embodiments, all penetrating radiation of the source of radiation is at energies below 70 keV. In some embodiments, the beam axis is perpendicular to the axis of rotation.

In some embodiments, there may be defined a plane that is transverse to the axis of rotation, and that intersects the emission point, such that the intersection of the axis of rotation with the plane is closer to the emission point than any point of intersection between the plane and the detector is to the emission point. In alternate embodiments, the axis of rotation is between and substantially equidistant from the emission point and a point of the detector that is closer to the emission point that any other point within the detector volume, and in yet other embodiments the detector is adjacent to the axis of rotation.

A movable backscatter inspection system for scanning a confined space, the detector includes a scanning platform rotatably coupled to a movable base, the scanning platform having an axis of rotation; a first source of a pencil beam of penetrating radiation, the first source coupled to the scanning platform and arranged to transmit a first scanning beam having a first axis projecting outward from the axis of rotation, the first source operating at or below 70 keV; and a plurality of detectors coupled to the base and forming a perimeter around the axis of rotation.

In some embodiments, a second source of a pencil beam of penetrating radiation is coupled to the scanning platform and arranged to transmit a second scanning beam along the first axis but in a direction opposite the first scanning beam as the scan platform rotates, and the system includes a controller for selectively activating one or a subset of the plurality of detectors to detect backscatter radiation from the first radiation source and for selectively activating another of the plurality of detectors, or another subset of the plurality of detectors, to detect backscatter radiation from the second radiation source.

Some embodiments include a distance detector mounted to detect the distance between the radiation source and an object being scanned.

A movable backscatter inspection system for scanning a confined space includes a scanning platform rotatably coupled to a movable base, the scanning platform having an axis of rotation; a first source of a pencil beam of penetrating radiation, the first source coupled to the scanning platform and arranged to transmit a first scanning beam having a first axis projecting outward from the axis of rotation, the first source operating at or below 70 keV; a second source of a pencil beam of penetrating radiation, the second source coupled to the scanning platform and arranged to transmit a second scanning beam along the first axis but in a direction opposite the first scanning beam as the scan platform rotates, the second source operating at or below 70 keV; a plurality of detectors coupled to the base and forming a perimeter around the axis of rotation; and a controller for selectively activating one of (or a subset of) the plurality of detectors to detect backscatter radiation from the first radiation source and for selectively activating another of the plurality of detector (or another subset of the plurality of detectors) to detect backscatter radiation from the second radiation source.

A multiple aperture backscatter inspection system has a scanning platform rotatably coupled to a base, the scanning platform having an axis of rotation; a first source of a pencil beam of penetrating radiation, the first source coupled to the scanning platform and arranged to transmit a first scanning beam having a first axis projecting outward from the axis of rotation; a first detector coupled to the scanning platform and defining an alignment vector normal to the direction of first scanning beam, whereby the first detector rotates with the radiation source; a second source of a pencil beam of penetrating radiation, the second source coupled to the scanning platform and arranged to transmit a second scanning beam having a second axis projecting outward from the axis in a direction opposite the first scanning beam; and a second detector coupled to the scanning platform and defining a second alignment vector normal to the axis of the second scanning beam, whereby the second detector rotates with the second radiation source. In some embodiments, the first radiation source operates at a first energy, and the second radiation source operates at a lower energy.

A number of other embodiments could be defined based on the foregoing description. For example, a potential claims include the following:

P1. A movable backscatter inspection system for inspecting contents of a space confined by an enclosure (which could be a metal enclosure, or could be another naturally-occurring space, such as a cave for example, or could be some other human-made metallic or non-metallic structure), the system comprising:
 a movable base;
 a scanning platform rotatably coupled to the base, the scanning platform having an axis of rotation;
 a source of radiation characterized by an energy spectrum, the source coupled to the scanning platform and arranged to emit a pencil beam of penetrating radiation from an emission point, the beam having a beam axis projecting outward from the axis of rotation, photoelectric attenuation of the penetrating radiation by the metal enclosure exceeding scattering of the penetrating radiation by the metal enclosure over the entire energy spectrum of the penetrating radiation;
 a first detector characterized by a detector volume, the first detector coupled to the scanning platform at a location such that the entire detector volume is closer to the axis of rotation of the scanning platform than the emission point is to the axis of rotation of the scanning platform, whereby the first detector rotates with the radiation source. [see, for example, FIG. 10, FIG. 11]

P2. A movable backscatter inspection system according to potential claim P1, wherein all penetrating radiation of the source of radiation is at energies below 70 keV.

P3. The movable backscatter inspection system of potential claim P1, wherein the beam axis is perpendicular to the axis of rotation.

P4. The movable backscatter inspection system of potential claim P1, wherein, in a plane that is transverse to the axis of rotation and intersects the emission point, the intersection of the axis of rotation with the plane is closer to the emission point than any point of intersection between the plane and the detector is to the emission point.

P5. The movable backscatter inspection system of potential claim P1, wherein the axis of rotation is between and substantially equidistant from the emission point and a point of the detector that is closer to the emission point that any other point within the detector volume.

P6. The movable backscatter inspection system of potential claim P1, wherein the detector is adjacent to the axis of rotation.

P7. A movable backscatter inspection system for scanning a confined space, the detector comprising:
 a movable base;
 a scanning platform rotatably coupled to the base, the scanning platform having an axis of rotation;
 a first source of a pencil beam of penetrating radiation, the first source coupled to the scanning platform and arranged to emit a first scanning beam having a first axis projecting outward from the axis of rotation, the first source operating at or below 70 keV;
 a plurality of detectors coupled to the base and forming a perimeter around the axis of rotation. [see, for example, FIG. 9]

P8. The movable backscatter inspection system of potential claim P7, further comprising:
 a second source of a pencil beam of penetrating radiation, the second source coupled to the scanning platform and arranged to emit a second scanning beam along the first axis but in a direction opposite the first scanning beam as the scan platform rotates;
 a controller for selectively activating one of, or a subset of, the plurality of detectors to detect backscatter radiation from the first radiation source and for selectively activating another of the plurality of detectors, or another subset of the plurality of detectors, to detect backscatter radiation from the second radiation source. [see, for example, FIG. 11]

P9. The movable backscatter inspection system of potential claim P7, further comprising a distance detector mounted to detect the distance between the radiation source and an object being scanned.

P10. A movable backscatter inspection system for scanning a confined space, the detector comprising:
 a movable base;
 a scanning platform rotatably coupled to the base, the scanning platform having an axis of rotation;
 a first source of a pencil beam of penetrating radiation, the first source coupled to the scanning platform and arranged to emit a first scanning beam having a first axis projecting outward from the axis of rotation, the first source operating at or below 70 keV;
 a second source of a pencil beam of penetrating radiation, the second source coupled to the scanning platform and arranged to emit a second scanning beam along the first axis but in a direction opposite the first scanning beam as the scan platform rotates, the second source operating at or below 70 keV;
 a plurality of detectors coupled to the base and forming a perimeter around the axis of rotation;
 a controller for selectively activating one or a subset of the plurality of detectors to detect backscatter radiation from the first radiation source and for selectively activating another of the plurality of detectors, or another subset of the plurality of detectors, or to detect backscatter radiation from the second radiation source. [see, for example, FIG. 11]

P11. A multiple aperture backscatter inspection system comprising:
 a base;
 a scanning platform rotatably coupled to the base, the scanning platform having an axis of rotation;
 a first source of a pencil beam of penetrating radiation, the first source coupled to the scanning platform and arranged to emit a first scanning beam having a first axis projecting outward from the axis of rotation;
 a first detector coupled to the scanning platform and defining an alignment vector normal to the direction of first scanning beam, whereby the first detector rotates with the radiation source;
 a second source of a pencil beam of penetrating radiation, the second source coupled to the scanning platform and arranged to emit a second scanning beam having a second axis projecting outward from the axis in a direction opposite the first scanning beam;
 a second detector coupled to the scanning platform and defining a second alignment vector normal to the axis of the second scanning beam, whereby the second detector rotates with the second radiation source. [see, for example, FIG. 10]

P12. The multiple aperture backscatter inspection system of potential claim P11, wherein the first radiation source operates at a first energy, and the second radiation source operates at a lower energy.

The embodiments of the invention described above are intended to be merely exemplary; numerous variations and modifications will be apparent to those skilled in the art. All such variations and modifications are intended to be within the scope of the present invention as defined in any appended claims.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods may be implemented as a computer program product for use with a computer system. Such implementation may include a series of computer instructions fixed either on a tangible medium, such as a non-transient computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments may be implemented as a combination of both software (e.g., a computer program product) and hardware. Still other embodiments of the invention are implemented as entirely hardware.

What is claimed is:

1. A movable backscatter inspection system for interrogating an object, the system comprising:
    a movable base;
    a source of a pencil beam of penetrating radiation, the source having an axis of emission and coupled to the base;
    a scan head coupled to the base, the scan head comprising at least one detector at a location not on the axis of emission and oriented to receive penetrating radiation scattered by the object; and
    a proximity sensor coupled to the base, and arranged to detect a predefined separation between the location and the object, the proximity sensor comprising:
        one of an acoustic sensor, mechanical sensor, or other contact sensor; and
        a bumper coupled to a mechanical sensor or other contact sensor.

2. The movable backscatter inspection system of claim 1 further comprising an indicator for alerting an operator when the predefined separation is detected, the indictor comprising at least one of a visual indicator and an audio indicator.

3. The movable backscatter inspection system of claim 1 further comprising brakes for slowing the motion of the base when the predefined separation is detected.

4. The movable backscatter inspection system of claim 1 further comprising brakes for stopping the motion of the base when the predefined separation is detected.

5. The movable backscatter inspection system of claim 1, the proximity sensor comprising a plurality of acoustic sensors.

6. A movable backscatter inspection system for interrogating an object, the detector comprising:
    a movable base;
    a source of a pencil beam of penetrating radiation, the source having an axis of emission and coupled to the base;
    a scan head coupled to the base, the scan head comprising at least one detector at a location not on the axis of emission and oriented to receive penetrating radiation scattered by the object; and
    a proximity sensor coupled to the base, and arranged to detect a predefined separation between the location and the object, the at least one proximity sensor comprising a bumper coupled to a mechanical sensor or other contact sensor.

7. The movable backscatter inspection system of claim 6, the proximity sensor comprising one of an acoustic sensor, mechanical sensor, or other contact sensor.

8. The movable backscatter inspection system of claim 6, the proximity sensor comprising an infrared sensor.

9. The movable backscatter inspection system of claim 6, the proximity sensor comprising an ultrasonic sensor.

10. The movable backscatter inspection system of claim 6, the proximity sensor comprising a capacitive sensor.

11. The movable backscatter inspection system of claim 6 further comprising an indicator for alerting an operator when the predefined separation is detected, the indictor comprising at least one of a visual indicator and an audio indicator.

12. The movable backscatter inspection system of claim 6 further comprising brakes for slowing the motion of the base when the predefined separation is detected.

13. The movable backscatter inspection system of claim 6 further comprising brakes for stopping the motion of the base when the predefined separation is detected.

14. The movable backscatter inspection system of claim 6, the proximity sensor comprising a plurality of acoustic sensors.

* * * * *